United States Patent [19]

Huland et al.

[11] Patent Number: 5,399,341

[45] Date of Patent: Mar. 21, 1995

[54] USE OF CYTOKIN-CONTAINING AEROSOLS AND THE CYTOKIN-CONTAINING AEROSOLS

[76] Inventors: Edith Huland; Hartwig Huland, both of Krottnaurerstrasse 50, D-1000 Berlin 38, Germany

[21] Appl. No.: 717,824

[22] Filed: Jun. 19, 1991

[30] Foreign Application Priority Data

Jun. 21, 1990 [EP] European Pat. Off. ........... 90111717

[51] Int. Cl.$^6$ ............................................. A61K 9/12
[52] U.S. Cl. .................... 424/45; 424/43; 424/450; 424/85.1; 424/85.2
[58] Field of Search ............. 424/85.1, 450, 43, 45, 424/85.2

[56] References Cited

U.S. PATENT DOCUMENTS

| | | | |
|---|---|---|---|
| 5,011,678 | 4/1991 | Wang et al. | 424/45 |
| 5,037,644 | 8/1991 | Shaked et al. | 424/85.2 |
| 5,049,389 | 9/1991 | Ladhakrishnan | 424/434 X |
| 5,162,507 | 11/1992 | Wolfe et al. | 530/412 |

FOREIGN PATENT DOCUMENTS

| | | |
|---|---|---|
| 0122036 | 10/1984 | European Pat. Off. |
| 0173990 | 3/1986 | European Pat. Off. |
| 0193372 | 9/1986 | European Pat. Off. |
| 0257956 | 2/1988 | European Pat. Off. |
| 0251631 | 7/1988 | European Pat. Off. |
| 0333523 | 9/1989 | European Pat. Off. |
| 60-224616 | 11/1985 | Japan . |
| 62-207226 | 9/1987 | Japan . |
| 02124832 | 5/1990 | Japan . |

OTHER PUBLICATIONS

Cancer, vol. 58, pp. 2764–2772 (1986).
Lotze, M. T., et al, "Clinical Effects and Toxicity of Interleukin-2 in Patients With Cancer" Cancer 58: 2764, 1986.
Thompson, J. A., et al, "Recombinant Interleukin-2 Toxicity, Pharmacokinetics, and Immunomodulatory Effects in a Phase 1 Trial" Cancer Res. 47:4202, 1987.
West, W. H., et al, "Constant-Infusion Recombinant-Interleukin-2 in Adoptive Immunotherapy of Advanced Cancer" N. Engl. J. Med.: 898, 1987.
Lotze, M. T., et al, "High-Dose Recombinant Interleukin-2 in The Treatment of Patients with Disseminated Cancer" J.A.M.A. 256:3117, 1986.
Rosenberg, S. A., et al, "A Progress Report on the Treatment of 157 Patients with Advanced Cancer using Lymphokine-Activated Killer Cells and Interleukin-2 or High-Dose Interleukin-2 Alone" New Engl. J. Med. 316: 898, 1987.
Kucharz, E. J., et al. "Serum Inhibitors of Interleukin-2" Life Sci. 42: 1485, 1988.
Forni G., et al. "Tumor Immunotherapy by Local Injection of Interleukin-2 and Non-Reactive Lymphocytes", Prog. Exp. Tumor Res. 32: 187, 1988.
Gramatzki, M. et al, "Intralymphatic Interleukin-2 Treatment in Patients with Acquired Immunodeficiency Syndrome: Preliminary Experience in Three Case" Immunobiol. 172:438, 1986.
Bubenik, J. "Local immunotherapy of cancer with interleukin-2", Immunol. Let. 21: 267, 1989.
Lotze, M. T., et al. "Intraperitoneal Administration of Interleukin-2 in Patients with Cancer" Arch. Surg. 121: 1373, 1986.
Yasumoto, K., et al. "Induction of Lymphokine-activated Killer Cells by Intrapleural Instillations of Recombinant Interleukin-2 in Patients with Malignant Pleurisy Due to Lung Cancer" Cancer Res. 47: 2184, 1987.

(List continued on next page.)

Primary Examiner—Thurman K. Page
Assistant Examiner—Raj Bawa
Attorney, Agent, or Firm—Richard S. Roberts

[57] ABSTRACT

The invention provides a method of treating tumors by the use of cytokin-containing aerosols for inhalative application and immuno-activation or continuous-immuno regulation in tumor diseases. The invention further proposes the use of cytokin-containing substances for producing an aerosol medicinal preparation for inhalative application and immuno-activation or continuous immuno-regulation in tumor diseases.

9 Claims, No Drawings

OTHER PUBLICATIONS

Rosenberg, S. A. "Immunotherapy of Cancer by Systemic Admin. of Lymphoid Cells Plus Interleukin-2", J. Biol. Resp Mod 3: 501, 1984.

Mittelman, A., et al, "Treatment of Patients with Advanced Cancer Using Multiple Long-Term Cultured Lymphokine-Activated Killer (LAK) Cell Infusions and Recombinant Human Interleukin-2", J. Biol. Resp. Mod. 8: 468, 1989.

Rosenberg, S. A. "Lymphokine-Activated Killer Cells: A New Approach to Immunotherapy of Cancer", J.N.C.I. 75: 595, 1985.

Paciucci, P. A., et al, "Recombinant Interleukin-2 by Continuous Infusion and Adoptive Transfer of Recombinant Interleukin-2-Activated Cells in Patients with Advanced Cancer", J. Clin. Oncol. 7: 869, 1989.

Grimm, E. A., et al, "Lymphokine-Activated Killer Cell Phenomenon", J. Exp. Med. 155: 1823, 1982.

Rosenberg, S. A. "Observations on the Systemic Administration of Autologous Lymphokine-Activated Killer Cells and Recombinant Interleukin-2 To Patients with Metastatic Cancer", N. Engl. J. Med. 313: 1485, 1985.

Belldegrun, A., "Lymphokines and activated cells in experimental and clinical immunotherapy" In: Immunotherapy of Urological Tumors (ed. deKernion JB), Churchill Livingston 1990.

USE OF CYTOKIN-CONTAINING AEROSOLS AND THE CYTOKIN-CONTAINING AEROSOLS

BACKGROUND OF THE INVENTION

The influencing of the immune response by a immune enhancement agent can decisively determine the course of the disease. This is particularly the case with malignant tumors, infections caused by fungi, viruses and parasites which cannot, or cannot adequately be given therapy, immuno-deficiency syndromes and by an immuno-suppression, e.g. in the case of foreign body transplants, autoimmune diseases or inflammatory diseases.

Cytokins are able to stimulate cells of the immune system in such a way as to act in the immune process in an immuno-activating or immuno-suppressing manner.

Despite the excellent perspectives with respect to the treatment of therapy resistant and infectious diseases, considerable problems are encountered during the administration or application of such cytokins.

The immuno-reaction provided by cytokins is difficult to control through the supply of exogenous cytokins. Only a rough immuno-response control is possible with the heretofore used systemic application processes (intravenous, intramuscular or subcutaneous cytokin administration). A further important disadvantage of the heretofore conventional systemic cytokin therapy is the extremely severe side effects, which lead to treatment only being possible with particularly good patients, who must in part be treated in intensive care units.

Interleukin-2, interferon and the tumor necrosis factor have been particularly well tested in this connection. However, other cytokins are in experimental use.

Systemic side effects such as fever, shivers, nausea, vomiting, diarrhea, life-threatening effects on the cardiovascular system such as heterotonia (varying blood pressure), dysrhythmia and the much feared capillary leakage syndrome, i.e. water retention due to a vascular sealing loss, are accompanying phenomena of systemic immuno-enhancement by cytokins. These are discussed in: Lotze, M. T., et al, "Clinical Effects and Toxicity of Interleukin-2 in Patients With Cancer" Cancer 58: 2764, 1986; Thompson, J. A., et al, "Recombinant Interleukin-2 Toxicity, Pharmacokinetics, and Immunomodulatory Effects in a Phase 1 Trial" Cancer Res. 47: 4202, 1987; West, W. H., et al, "Constant-Infusion Recombinant-Interleukin-2 in Adoptive Immunotherapy of Advanced Cancer" N.Engl.J.Med.: 898, 1987; Lotze, M. T., et al, "High-Dose Recombinant Interleukin-2 in the Treatment of Patients with Disseminated Cancer" J.A.M.A. 256: 3117, 1986; Rosenberg, S. A., et al, "A Progress Report on the Treatment of 157 Patients with Advanced Cancer using Lymphokine-Activated Killer Cells and Interleukin-2 or High-Dose Interleukin-2 Alone" New Engl.J.Med. 316: 898, 1987; and Lotze, M. T., et al, "High-Dose Recombinant Interleukin-2 in the Treatment of Patients With Disseminated Cancer" J.A.M.A. 256: 117, 1986.

In addition, systemic therapy is made more difficult by the fact that cytokins are rapidly eliminated from the blood. For example, interleukin-2 has a half-life in the blood of 13 minutes. A further problem is that the blood contains powerful cytokin inhibitors. (See Kucharz, E. J., et al. "Serum Inhibitors of Interleukin-2" Life Sci. 42: 1485, 1988).

Local administration of cytokins leads to far fewer side effects. In this regard see Forni G., et al. "Tumor Immunotherapy by Local Injection of Interleukin-2 and Non-Reactive Lymphocytes", Prog. Exp. Tumor Res. 32: 187, 1988; Gramatzki, M. et al, "Intralymphatic Interleukin-2 Treatment in Patients with Acquired Immunodeficiency Syndrome: Preliminary Experience in Three Cases" Immunobiol. 172: 438, 1986; Bubenik, J. "Local immunotherapy of cancer with interleukin-2", Immunol. Let. 21: 267, 1989; Lotze, M. T., et al. "Intraperitoneal Administration of Interleukin-2 in Patients with Cancer" Arch. Surg. 121: 1373, 1986; Yasumoto, K., et al. "Induction of Lymphokine-activated Killer Cells by Intrapleural Installations of Recombinant Interleukin-2 in Patients with Malignant Pleurisy Due to Lung Cancer" Cancer Res. 47: 2184, 1987. However at present no use is made thereof, because there is almost always a systemic disease at hand, such as metastasized tumor, generalized immune deficiency (AIDS) and autoimmune diseases and adequate immuno-stimulation is not brought about through a short term, local application. The technically complicated, expensive and patient-stressing method of adoptive infusion of immune cells has been employed as a way out. In this regard see Rosenberg, S. A. "Immunotherapy of Cancer by Systemic Administration of Lymphoid Cells Plus Interleukin-2", J. Biol. Resp Mod 3: 501, 1984; Mittelman, A., et al, "Treatment of Patients with Advanced Cancer Using Multiple Long-Term Cultured Lymphokine-Activated Killer (LAK) Cell Infusions and Recombinant Human Interleukin-2", J Biol Resp. Mod. 8: 468, 1989; Rosenberg, S. A. "Lymphokine-Activated Killer Cells: A New Approach to Immunotherapy of Cancer", J.N.C.I. 75: 595, 1985; Paciucci, P. A., et al, "Recombinant Interleukin-2 by Continuous Infusion and Adoptive Transfer of Recombinant Interleukin-2-Activated Cells in Patients with Advanced Cancer", J. Clin. Oncol. 7: 869, 1989; Grimm, E. A., et al, "Lymphokine-Activated Killer Cell Phenomenon", J. Exp. Med. 155: 1823, 1982; Rosenberg, S. A. "Observations on the Systemic Administration of Autologous Lymphokine-Activated Killer Cells and Recombinant Interleukin-2 To Patients with Metastatic Cancer", N.Engl.J.Med. 313: 1485, 1985; Belldegrun, A., "Lymphokines and activated cells in experimental and clinical immunotherapy" In: Immunotherapy of Urological Tumors (ed. deKernion JB), Churchill-Livingston 1990.

Endogenic immune cells have been taken from the patient (cf. FIG. 24.1 in Belldegrun, ibid.), which are either cells from the blood, which are non-specifically stimulatable, or immune cells are directly obtained from the tumor, i.e. from the diseased or affected area, which are specifically stimulatable against antigens.

These immune cells are then mixed with corresponding cytokins in vitro, i.e. in the test tube and are replaced after successful stimulation. This involves considerable effort and expenditure, above-average quantities of equipment and specially trained staff (cf. FIG. 24.2 in Belldegrun, ibid.).

The taking of these immune cells involves an infection risk for the patient. The re-infusion can also represent an infection source for the patient (hepatitis transmission has been reported). As the cells are firstly taken from the patient and then stimulated in vitro, in the case of repeated therapy cycles, intervals occur between the individual therapies, which is not desired with such diseases. For these and other reasons, the aforementioned application cannot be used as a long-term process lasting months or even years. However, a long-term application is the prerequisite for effective immunotherapy.

The problem which the invention seeks to solve is to develop a cytokin application, which can continuously extend over a long period, i.e. months to years, which has few side effects and which still has a powerful systemic action. Application must be simple and rapidly performable for the patient, without requiring equipment or processes which are complicated with regard to technology and personnel.

According to the invention this problem is surprisingly solved by the use of cytokin-containing aerosols for inhalative application and immuno-activation or continuous immuno-regulation in tumor diseases or the use of cytokin-containing substances for producing an aerosol medicinal preparation for inhalative application and immuno-activation or continuous immuno-regulation in tumor diseases, and by daily doses between approximately 2 and 5×100,000 U BRMP, 2 and 5×200,000 U BRMP, 5×300,000 U BRMP, particularly 5×100,000 U BRMP and 5×200,000 U BRMP.

The inhalative application of medicaments is not novel per se. However, this has hitherto involved the use of other medicaments and with completely different aims, e.g. asthma patients or allergic persons e.g. inhale substances during an acute pulmonary disease, e.g. for expectoration purposes. In the case of AIDS patients, antibiotics are applied by inhalation, to avoid local infection risks.

However, the inventive concept of obtaining a systemic action, in that the large local surface of approximately 100m$^2$ of the lung is utilized in order to activate immune cells reachable on this surface, and to make the same available to the circulatory system, satisfies a long-standing need for achieving very high tumor regression throughout the body by simple application or administration.

Equally novel and characteristic for the inventive use of cytokin-containing aerosols is the advantageous use over many months and daily application for many days. This combination induces an optimum, continuous immuno-stimulation, which cannot be achieved as efficiently and without side effects in any other way. The effectiveness can not only be measured through the regression of metastases, but also on the cytotoxicity of the stimulated cells.

The analysis of the inventively obtained cytotoxicity shows a clearly increased tumor toxicity of the immune cells present in the blood, and also in the phase when the ambulatory patient only receives an inhalative cytokin application and not a systemic application. This high effectiveness and extremely good compatibility could not have been foreseen.

Interleukin-2 systemically brings about a considerable liquid incorporation, so that intravenously treated patients have a considerable risk of a pulmonary edema developing. The inventive application form by aerosol inhalation has not as yet revealed this side effect in patients. A dosage increase has only led to the occurrence of moderate systemic effects (fever, blood pressure reduction, etc.).

Cytokins have been available in unpurified form for decades. For roughly ten years gene-technologically produced and well characterized cytokins have been available.

Although the application form of cytokins has been intensely discussed in smaller and also larger research, cytokin aerosol application has not been as yet considered anywhere in the world. There are two main reasons for this. Firstly, such an impressive systemic immuno-stimulation could not be expected through this local application form and secondly, significant and much more dangerous side effects were expected, namely pulmonary edema, and the induction of lung allergies, etc.

A further possible reason might be that no data was available giving information on the stability and penetrability of cytokins in the form of an aerosol application. Aerosol production equipment has long been known. However, cytokin aerosol application has never been considered.

The inventive inhalative application form with cytokin-containing aerosols has already proved very effective within the scope of a pilot study in the case of patients with incurable carcinomas.

Advantageously the cytokin decisive for immuno-activation, i.e. interleukin-2, is applied to the patient by inhalation as an aerosol several times daily.

The hitherto well accepted doses may vary between 2 and 5×100,000 U BRMP and experience exists with dosage increases up to 5×300,000 U BRMP/day. Two patients have been treated with this inhalative application for six months and have surprisingly revealed no side effects in the lungs.

SUMMARY OF THE INVENTION

The invention provides for the use of cytokin-containing aerosols for inhalative application and immuno-activation or continuous immuno regulation in tumor diseases, therapy-resistant infections, immunodeficiency syndromes, foreign body transplants, autoimmune diseases and therapy-resistant, inflammatory diseases.

The invention also provides for the use of cytokin-containing substances for producing an aerosol medicinal preparation for inhalative application and immuno-activation or continuous regulation in tumor diseases, therapy-resistant infections, immunodeficiency syndromes, foreign body transplants, autoimmune diseases and therapy-resistant, inflammatory diseases.

The invention furthermore provides for an aerosol composition capable of being administered to patients in inhalable form, which composition comprises a cytokin and a pharmaceutically acceptable carrier therefor.

The invention still further provides for a method for treating patients having infections, immunodeficiency syndromes, inflammatory diseases, autoimmune diseases, foreign body transplants, or requiring immuno regulation of tumor diseases, which method comprises causing such a patient to inhale an aerosol composition, which aerosol composition comprises a cytokin and a pharmaceutically acceptable carrier therefor.

DETAILED DESCRIPTION OF THE PREFERRED EMBODIMENT

Interleukin administration takes place with an atomizer, which produces very small droplets and therefore ensures an optimum distribution over the lung surface. In addition, a pre-atomization with a buffer albumin solution is advantageous, to avoid adhesion of the cytokin to the surface of the tube system. This application form could even be used during a short, clinical preliminary period in ambulatory manner and consequently offers a possibility of long-term therapy. Existing data shows that this application form is not only patient-friendly, i.e. very compatible in that it has virtually no side effects for a dosage of approximately 5×200,000 U BRMP, but is also extremely effective.

In one preferred embodiment as an aerosol, the medicament can have the following composition: Interleukin-2 100,000 U BRMP/ml in 0.1% (wt/vol) human serum albumin, 0.01M phosphate buffer with 0.15M NaCl, pH 7.4. As a function of the desired application quantity, a higher interleukin-2 concentration per ml can be chosen. The buffer solution can also be replaced by a physiological common salt solution, without any limitations being feared. Alternatively comparable buffer solutions can be used.

The pre-atomization solution is not applied to the patient and instead merely serves to block protein binding points in the tube system, so that here interleukin-2 is not non-specifically bound and lost for patient therapy.

The clinical effects are discussed hereinafter relative to two patients.

EXAMPLE 1

A first patient has a metastasized kidney tumor. Initial diagnosis took place in October 1989 as tumor nephrectomy. At this time there was considerable metastasization of the tumor in the lungs with functional impairment of the lung in the form of dyspnea. This was followed by systemic interferon-alpha therapy under which the tumor progressed in measurable form. Systemic interleukin-2 therapy began in December 1989. With unchanged severe metastasization in January 1990, there was increasing weight loss (from 80 to 54 kg) and increasing dyspnea (breathlessness even when speaking). This was supplemented by daily multiple interleukin inhalation as described above. There was a clear tumor regression as shown by X-rays of the thorax. During therapy the weight increased, up to now by 12 kg, to 66 kg. Clearly increased fitness of the patient and in particular no further dyspnea are observed.

EXAMPLE 2

A second patient had a metastasized renal cell carcinoma. The initial diagnosis revealing tumor nephrectomy took place in October 1988, metastases not being detected then. A computer tomograph first revealed local lymph node metastases, as well as enlarged lymph nodes in the mediastinum and several lung metastases in September 1989. Interferon-alpha therapy started in November 1989 and was accompanied by systemic interleukin-2 therapy due to further tumor progression. There was no reduction in the tumor metastases and therefore it was decided to give inhalative cytokin application with interleukin-2. Within 3 weeks there was regression of the lung metastase and clear reduction of the mediastinal and regional lymph node metastases during the following 3 months. Therapy has lasted 6 months up to now.

Both treated patients are still in a phase of continual tumor regression, so that they are on the best path to full remission. The improvement to the quality of life, the weight increase and the disappearance of dyspnea in patient 1 are largely due to the inhalative application and not or only to a limited extent to the intravenous application. It is to be expected that other cytokins, besides interleukin-2, will be equally effective.

This readily controllable application form for cytokins can also be used for other diseases, which can be influenced by cytokins, inter alia immunodeficiency syndromes, therapy-resistant infections, foreign body transplants, autoimmune diseases and therapy-resistant, and inflammatory diseases.

What is claimed is:

1. A method of administrating to patients having infections, immunodeficiency syndromes, inflammatory diseases, autoimmune diseases, foreign body transplants, or requiring immuno regulation of tumor diseases, which method comprises causing such a patient to inhale an aerosol composition, which aerosol composition consists essentially of a solution of a cytokin and a pharmaceutically acceptable carrier therefor wherein the pharmaceutically acceptable carrier is human serum albumen and a component selected from the group consisting of one or more of a pharmaceutically acceptable salt solution, and a pharmaceutically acceptable buffer.

2. The method of claim 1 wherein the cytokin is interleukin-2.

3. The method of claim 1 wherein the composition is administered to the patient a plurality of times daily.

4. The method of claim 3 wherein the composition is substantially uniformly administered to the patient for a plurality of months.

5. The method of claim 1 wherein the composition is administered to the patient by means of an atomizer producing atomized droplets of the composition.

6. The method of claim 1 wherein the composition is administered to the patient in daily doses in the range of from about 2 to about 5 times 100,000 U BRMP.

7. The method of claim 1 wherein the composition is administered to the patient in daily doses in the range of from about 2 times 100,000 U BRMP to about 5 times 300,000 U BRMP.

8. The method of claim 1 wherein the pharmaceutically acceptable carrier is human serum albumen and a component selected from the group consisting of one or more of a sodium chloride solution, and a phosphate buffer solution.

9. The method of claim 1 wherein the pharmaceutically acceptable carrier is a mixture of human serum albumen a sodium chloride solution and a phosphate buffer solution.

* * * * *